(12) United States Patent
Kim

(10) Patent No.: US 10,070,872 B2
(45) Date of Patent: Sep. 11, 2018

(54) MEDICAL MOTOR DRILL WITH ANGLE ADJUSTING FUNCTION

(71) Applicant: THE CATHOLIC UNIVERSITY OF KOREA INDUSTRY-ACADEMIC COOPERATION FOUNDATION, Seoul (KR)

(72) Inventor: Jae Jun Kim, Seoul (KR)

(73) Assignee: THE CATHOLIC UNIVERSITY OF KOREA INDUSTRY-ACADEMIC COOPERATION FOUNDATION, Seoul (KR)

( * ) Notice: Subject to any disclaimer, the term of this patent is extended or adjusted under 35 U.S.C. 154(b) by 196 days.

(21) Appl. No.: 14/759,230

(22) PCT Filed: Apr. 30, 2015

(86) PCT No.: PCT/KR2015/004420
§ 371 (c)(1),
(2) Date: Dec. 19, 2016

(87) PCT Pub. No.: WO2015/167291
PCT Pub. Date: Nov. 5, 2015

(65) Prior Publication Data
US 2017/0112506 A1    Apr. 27, 2017

(30) Foreign Application Priority Data

May 2, 2014    (KR) ........................ 10-2014-0053338

(51) Int. Cl.
*A61B 17/16*        (2006.01)
*A61B 17/00*        (2006.01)

(52) U.S. Cl.
CPC .... *A61B 17/1631* (2013.01); *A61B 17/00234* (2013.01); *A61B 17/1613* (2013.01);
(Continued)

(58) Field of Classification Search
CPC . A61B 17/16; A61B 17/1613; A61B 17/1615; A61B 17/162; A61B 17/1622;
(Continued)

(56) References Cited

U.S. PATENT DOCUMENTS

| 7,743,683 B2 * | 6/2010 | Dayton | ..................... B25F 3/00 |
| | | | 173/216 |
| 7,752,760 B2 * | 7/2010 | Baskar | ................. A01G 3/0417 |
| | | | 30/210 |
| 8,348,959 B2 * | 1/2013 | Wolford | ............. A61B 17/1624 |
| | | | 606/104 |

FOREIGN PATENT DOCUMENTS

| KR | 20-0258553 Y1 | 12/2001 |
| KR | 20-0353691 Y1 | 6/2004 |

(Continued)

OTHER PUBLICATIONS

International Search Report for PCT/KR2015/004420 , dated May 11, 2015.

*Primary Examiner* — Larry E Waggle, Jr.
(74) *Attorney, Agent, or Firm* — The PL Law Group, PLLC

(57) ABSTRACT

Disclosed is a medical motor drill having an angle adjusting function. The medical motor drill includes a main body, a shaft connected to the main body, a drill unit connected to the shaft so as to be bendable relative to the shaft, the drill unit including a motor configured to receive power from the main body and a drill blade configured to be rotated by the motor, a drive force transmission unit configured to bend the drill unit relative to the shaft, and an angle adjustment unit connected to the drive force transmission unit to adjust a bending degree of the drill unit. The medical motor drill has advantages of enabling drilling over a wide range in a state in which a drill manipulation position is fixed and of (Continued)

enabling adjustment in the angle of the drill unit that is located distant from a user manipulation position.

5 Claims, 5 Drawing Sheets

(52) U.S. Cl.
CPC *A61B 17/1622* (2013.01); *A61B 2017/00398* (2013.01); *A61B 2017/00415* (2013.01)

(58) Field of Classification Search
CPC ... A61B 17/1631; B23B 45/00; B23B 45/005; B23B 2260/068; B23B 2270/06; B25F 5/00
See application file for complete search history.

(56) References Cited

FOREIGN PATENT DOCUMENTS

| | | |
|---|---|---|
| KR | 10-2011-0044470 A | 4/2011 |
| KR | 10-2011-0092736 A | 8/2011 |
| WO | 98-18394 A1 | 5/1998 |

\* cited by examiner

MEDICAL MOTOR DRILL WITH ANGLE ADJUSTING FUNCTION

TECHNICAL FIELD

The present invention relates to a medical motor drill for use in a thoracic surgery and, more particularly, to a medical motor drill which allows medical staff to adjust an angle of the drill inserted into the thoracic cavity from the outside of the thoracic cavity.

BACKGROUND ART

In recent years, various accidents, caused by industrialization, structural instability in society and variation in living conditions, increase trauma patients at home and abroad. Thoracic injuries due to traumas need to be rapidly and appropriately diagnosed and treated because organs having a direct effect on life are located in the thoracic cavity. Such thoracic injuries are mainly caused by acceleration and collision of the human body such as in car accidents and falling accidents. The most common thoracic trauma is rib fracture. Rib fracture patients require appropriate treatment because even fracture of a single rib may cause damage to organs inside the thoracic cavity such as, for example, hematothorax and pneumothorax, as well as abdominal organ damage.

As known from conventional researches and the like, damage to multiple ribs, i.e. multiple rib fracture is the most common thoracic injury. Conventionally, conservative treatment for rib fracture has been implemented to achieve efficient lung ventilation at an injury site and to prevent complications such as, for example, atelectasis and pneumonia. In the case of thoracic injury, however, conservative treatment requires longer term hospitalization than surgical treatment and does not case rehabilitation after the end of hospital treatment, whether or not return to daily life is possible, or aftereffects such as, for example, continuous pain. To solve the problems as described above, a variety of researches on rib fracture has recently been conducted. Such researches show that surgical treatment is superior to general conservative treatment in terms of economic and medical opinions.

A conventional surgical treatment method includes making an incision in the chest, placing a rib plate at a fractured rib, and fixing the lip plate using a screw to correct the rib. However, a conventional motor drill is devised to provide only vertical external force when fixing the screw and thus has the following limits. First, when making an incision in the chest for surgery, the single incision permits correction of only two or three ribs at and near the incision. Thus, making numerous incisions in the chest with a general rib fracture surgical method is practically difficult, which makes it impossible to correct multiple fractures throughout front, lateral and rear walls of the chest. Second, when ribs below the shoulder blade are damaged, direct rib correction is impossible due to the shoulder blade even if an incision is made. Third, although thoracotomy is required when serious traumas cause damage to internal organs or ribs are double fractured and invade the thoracic cavity, thoracotomy problematically puts the patient in greater danger in a state in which the walls of the chest are damaged. In addition, correcting all target ribs may be impossible despite implementation of thoracotomy.

To solve the problems as described above, there is a demand for surgical methods and medical instruments which are capable of correcting a plurality of ribs through a topical incision. More specifically, in order to perform a surgical method capable of correcting a plurality of ribs through a topical incision, a medical motor drill is necessary, which is configured to be inserted through the topical incision and serves to fix a lip plate to any of ribs at front, lateral, and rear walls of the chest.

Conventionally, there is present no medical motor drill which allows medical staff to adjust an angle of the motor drill inserted through a topical incision to fix a lip plate and, therefore, surgical treatment of multiple rib fracture is not possible.

Reference is made to Korean Utility Model Registration Publication No. 20-0258553 as the related art of a hand drill.

DISCLOSURE

Technical Problem

Therefore, the present invention has been made in view of the above problems, and it is an object of the present invention to provide a medical motor drill which is adjustable in angle. In addition, it is another object of the present invention to provide a medical motor drill which allows a user to adjust an angle of a drill unit that is distant from a user manipulation position. Accordingly, it is a further object of the present invention to provide a medical motor drill which is adjustable in angle in a state in which the drill is inserted through a topical incision, thereby enabling correction of ribs.

Technical Solution

In accordance with one aspect of the present invention, to accomplish the above and other objects, there is provided a medical motor drill including a main body, a shaft connected to the main body, a drill unit connected to the shaft so as to be bendable relative to the shaft, the drill unit including a motor configured to receive power from the main body and a drill blade configured to be rotated by the motor, a drive force transmission unit configured to bend the drill unit relative to the shaft, and an angle adjustment unit connected to the drive force transmission unit to adjust a bending degree of the drill unit. In this case, the angle adjustment unit may be located at the main body.

Advantageous Effects

As described above, in accordance with the present invention, the present invention has an advantage of enabling drilling over a wide range in a state in which a drill manipulation position is fixed. In addition, the present invention has an advantage of enabling adjustment in the angle of a drill unit that is located distant from a user manipulation position. Accordingly, the present invention has an advantage of correcting a rib by adjusting the angle of the drill inserted through a topical incision. When the medical motor drill according to the present invention is used in thoracic cavity surgery, it requires an incision having a diameter of about 2 cm or less, which is remarkably smaller than a diameter (about 10 cm or more) of a general chest incision, thereby achieving an aesthetic advantage. In addition, correction of all ribs through a single incision is possible regardless of a position of the incision, which enables surgical treatment of multiple rib fracture which was impossible in the related art.

BEST MODE

Figure 1A:
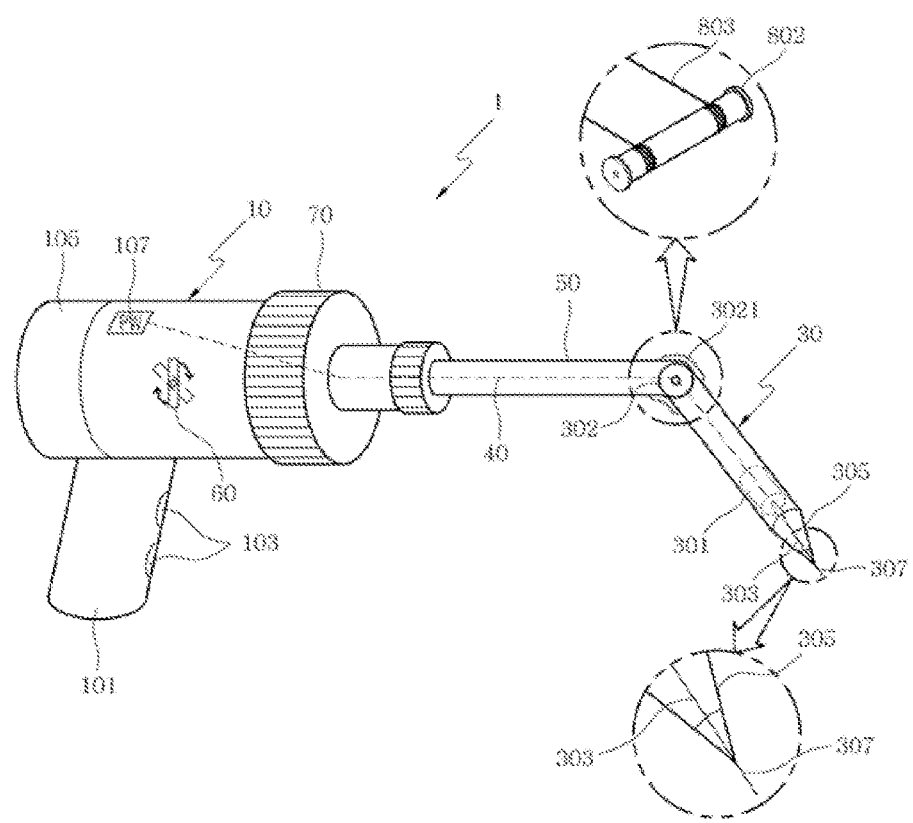
FIGS. 1A and 1B illustrate medical motor drills according to respective exemplary embodiments of the present invention.

Hereinafter, the present invention will be described in detail with reference to illustrations of the accompanying drawings. However, it will be appreciated that the present invention is not limited or constrained by the exemplary embodiments. Throughout the drawings, the same reference numerals denote substantially the same functional members.

Figure 1B:
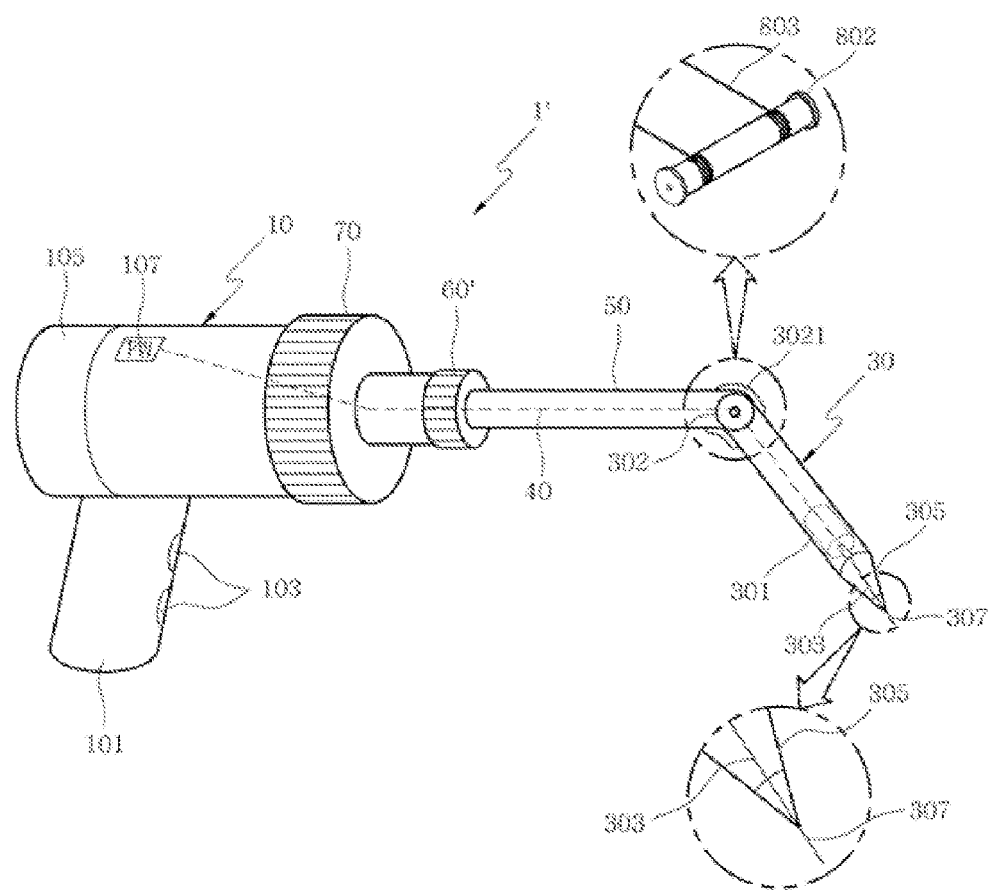

FIGS. 1A and 1B illustrate medical motor drills 1 and 1' according to respective exemplary embodiments of the present invention. FIG. 1A illustrates the medical motor drill 1 in which an angle adjustment unit 60 is placed at a main body 10 and FIG. 1B illustrates the medical motor drill 1' in which an angle adjustment unit 60' is placed at a shaft 50.

Referring to FIGS. 1A and 1B, the medical motor drills 1 and 1' respectively include the main body 10 comprised of a battery 105, a handle 101, a power source 107 and switches 103, the shaft 50 connected to the main body 10, a drill unit 30 having a motor 301 to receive power through a conductor 40 and a drill blade 303 adapted to be rotated by the motor 301, the drill unit 30 being connected to the shaft 60 so as to be bendable relative to the shaft 50, and the angle adjustment unit 60 or 60' to adjust a bending degree of the drill unit 30.

The power source 107 is mounted in the main body 10 and power generated by the power source 107 is used to rotate the motor 301 forward or in reverse based on operation of the switch 103. In this case, the motor 301 is adapted to tighten or loosen a screw by rotating the drill blade 303 connected to the motor 301 forward or in reverse.

Referring to FIG. 1A, the angle adjustment unit 60 in the form of a lever may be provided at a lateral surface of the main body 10 to bend the drill unit 30 via rotational operation thereof. Alternatively, as exemplarily illustrated in FIG. 1B, the angle adjustment unit 60' in the form of a knob may be located at one end of the shaft 50 connected to the main body 10.

The handle 101 is coupled to the bottom of the main body 10. In this case, the handle 101 may be provided at the top thereof with a hinge and coupled to the main body 10 to pivotally rotate in an arc path relative to the main body 10. This allows orientation of the handle 101 to correspond to a direction in which pressure is applied to bend the drill unit 30. Alternatively, the switch 103 may be located at the handle 101 or an opposite lateral surface (not shown) of the main body 10.

The shaft 50 may include a rotation adjustment unit 70 that is connected to the main body 10 and serves to rotate the shaft 50 about the longitudinal axis of the shaft 50 as a rotation axis. In the present exemplary embodiment, the rotation adjustment unit 70 may take the form of a knob and be rotatably coupled to an opening (108, see FIG. 3) of the main body 10. This will be described below with reference to FIG. 3.

The shaft 50 may be formed of a light and rigid material and, in the present exemplary embodiment, may be formed of titanium alloy. The shaft 50 may be extended to 20 cm or more so as to be inserted into the thoracic cavity. In addition, the shaft 50 should have a diameter suitable for insertion through a topical incision through which an endoscope will be inserted. Therefore, the diameter of the shaft 50 may be 2 cm or less. The shaft 50 has an inner cavity for passage of the conductor 40 and wires (803, see FIGS. 2A and 2B) that are used to connect the power source 107 and the motor 301 to each other.

The drill unit 30 accommodates the motor 301 and the drill blade 303 therein, and an end of the drill blade 303 is outwardly exposed to form a drill tip 307. In addition, the drill unit 30 may include a cap 305 that stably fixes the drill tip 307 to prevent shaking. In the present exemplary embodiment, the cap 305 may have a conical shape having a sharpened end. This serves to prevent the cap 305 from blocking the visual field of the drill tip 307 when the drill unit 30 is inserted, along with the endoscope, to the thoracic cavity for screwing.

The drill unit 30 may be provided at one end thereof with a connector 302 to enable bendable connection between the drill unit 30 and the shaft 50. A driven drum (802, see FIGS. 2A and 2B) may be connected to the inside of the connector 302. In addition, the connector 302 may be inserted into the shaft 50 and have a hinge to connect the shaft 50 and the drill unit 30 to each other. In this case, since the hinge protruding outward from the connector 302 may damage surrounding tissues during insertion of the shaft 50 into the thoracic cavity, a protective packing 3021 is provided to surround the periphery of the connector 302.

The drill unit 30 may be extendible by 5 cm or less for stable screwing because the drill unit 30 is spaced apart from the body 10 by a length of the shaft 50 when being inserted into the thoracic cavity. In addition, the drill unit 30 may have a diameter of 2 cm or less because the drill unit 30 should have a diameter for insertion through a topical incision through which an endoscope will be inserted. The drill tip 307 may be a magnetic tip that protrudes from the cap 305 by a length of up to 1 cm. This serves to ensure stable screwing of the fine drill blade 303 and to prevent unintentional separation of a screw that comes into close contact with the drill tip 307 due to gravity. The motor 301 may be a small, low output motor having an outer diameter of 2 cm or less in order to be mounted in the drill unit 30.

Figure 2A:
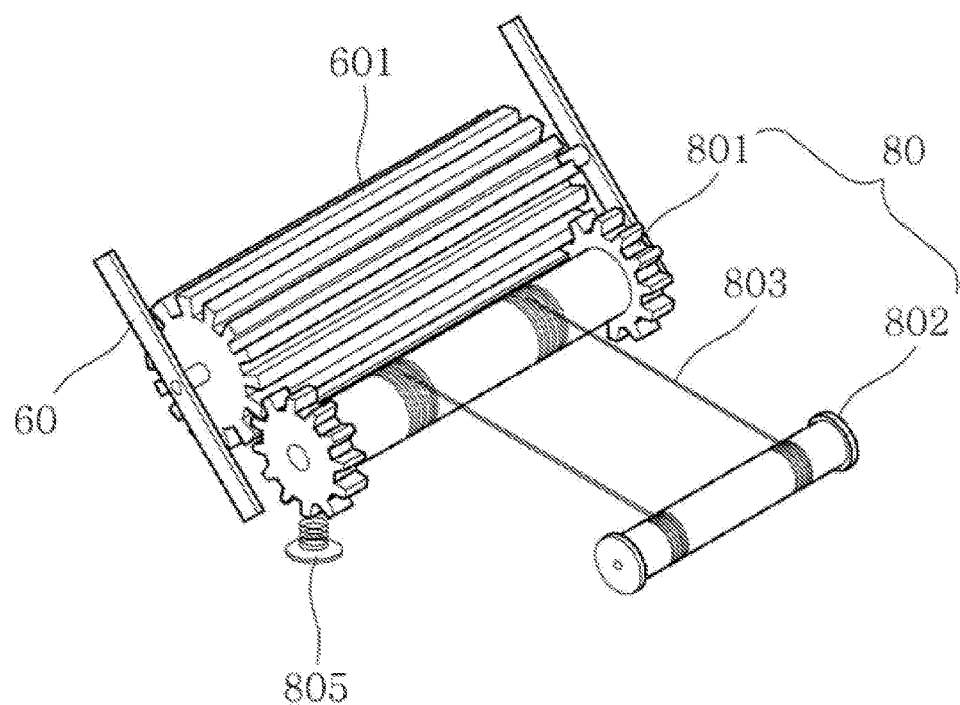
FIGS. 2A and 2B illustrate a drive force transmission unit and angle adjustment units included in the medical motor drills according to the respective exemplary embodiments of the present invention.
Figure 2B:
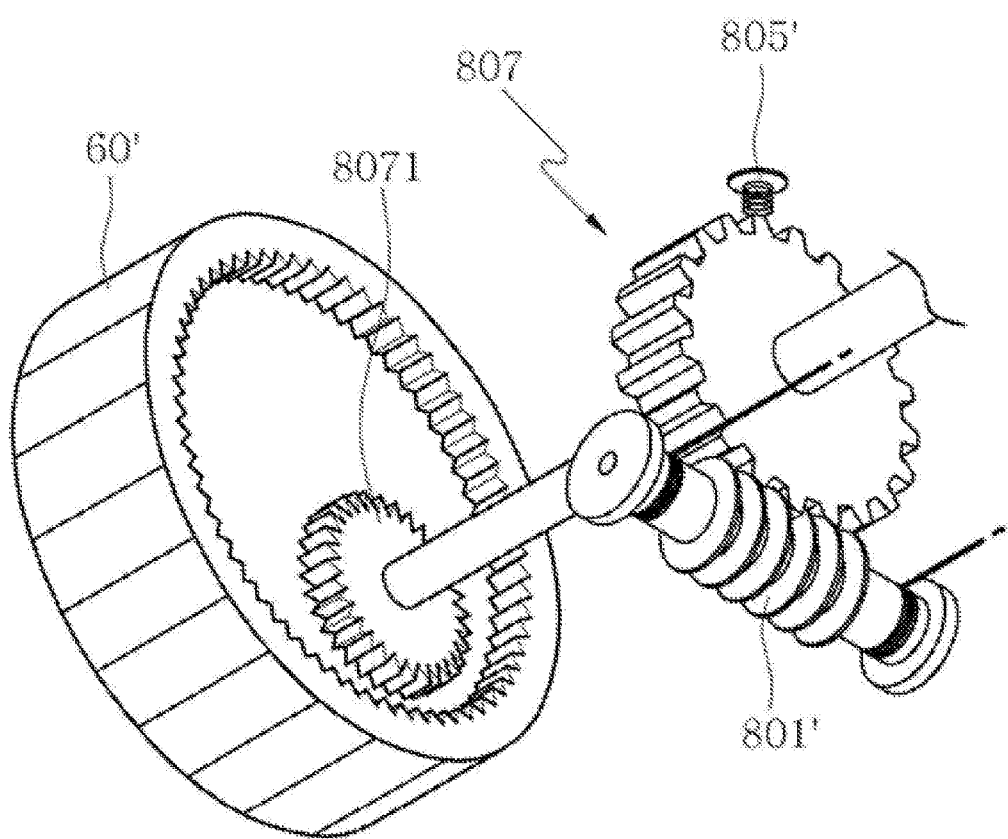

FIGS. 2A and 2B illustrates a drive force transmission unit 80 and the angle adjustment units 60 and 60'. Referring to FIGS. 2A and 2B, the drive force transmission unit 80 may include driving gears 801 to be rotated by the angle adjustment unit 60 or 60', the driven drum 802 connected to the drill unit 30, the wires 803 wound around the driving gears 801 and the driven drum 802, and a stopper 805 or 805' selectively fitted to a groove of a respective one of the driving gears 801. In the present exemplary embodiment, the stopper 805 or 805' may be a torsion spring that serves to fix the driving gear 801 by being selectively fitted to the groove of the driving gear 801.

FIG. 2A illustrates the angle adjustment unit 60 in the form of a lever and the drive force transmission unit 80. The angle adjustment unit 60 may include a toothed gear 601 engaged with the driving gears 801. The toothed gear 601 serves to transmit torque applied to the angle adjustment unit 60 to the driving gears 801. The wire 803 wound around a respective one of the driving gears 801 may serve to convert the torque applied to the driving gear 801 into horizontal external force and to transmit the same to the driven drum

802. The driven drum 802 connected to the drill unit 30 may serve to convert the horizontal external force applied from the wire 803 into torque required to bend the drill unit 30.

In the present exemplary embodiment, the angle adjustment unit 60 may be located at the main body 10. When the angle adjustment unit 60 is located at the main body 10, the toothed gear 601 and the driving gears 801 may be arranged inside the main body 10 and a lever portion of the angle adjustment unit 60 is outwardly exposed from the main body 10. The stopper 805 is located inside the main body 10 and selectively fitted to the groove of a respective one of the driving gears 801. The drive force transmission unit 80 may include an additional gear between the driving gears 801 and the toothed gear 601 in order to adjust a gear speed ratio of the driving gears 801.

Referring to FIG. 2B illustrating the angle adjustment unit 60' according to another exemplary embodiment, the angle adjustment unit 60' may take the form of a knob provided with teeth at an inner circumference thereof and a driving gear 801' may include a worm gear 807. In this case, the angle adjustment unit 60' may be located at one end of the shaft 50 toward the main body 10. In addition, the stopper 805' may be located inside the shaft 50 so as to be selectively fitted into a groove of the driving gear 801'. The driving gear 801' may have winding portions protruding from both ends thereof in opposite directions for winding of the wires 803.

In the case where the driving gear 801' includes the worm gear 807, the worm gear 807 may include an additional lo gear 8071 configured to be engaged with the teeth of the angle adjustment unit 60'. The drive force transmission unit 80 may include an additional gear between the driving gear 801' and the angle adjustment unit 60' in order to adjust a gear speed ratio of the driving gear 801'.

The drive force transmission unit 80, as described above, may include at least two gears connected respectively to the angle adjustment unit 60 or 60' and the drill unit 30 and may be a combination of gears to convert the direction of external force applied to the angle adjustment unit 60 or 60' into the direction of torque applied to the drill unit 30.

According to an exemplary embodiment, the angle adjustment units 60 and 60' may adjust an angle of the drill unit 30 about the shaft 50 within a range of −90 degrees to +90 degrees. In this case, the adjusted angle may be fixed by the stoppers 805 and 805'.

Figure 3:
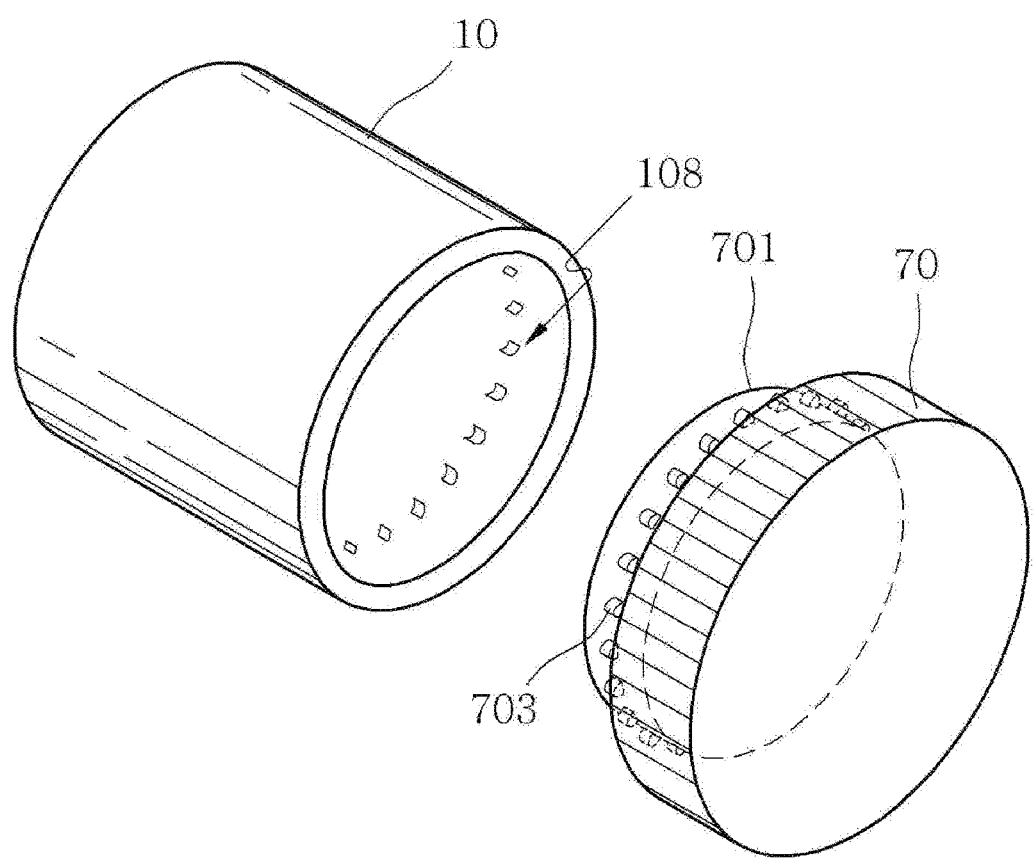
FIG. 3 illustrates a rotation adjustment unit included in the medical motor drill according to the exemplary embodiment of the present invention.

FIG. 3 illustrates the rotation adjustment unit 70. Referring to FIG. 3, the rotation adjustment unit 70 may be provided at the end of the shaft 50 coupled to the main body 10 to rotatably couple the shaft 50 to the main body 10. More specifically, the rotation adjustment unit 70 may rotate the shaft 50 about the longitudinal axis of the shaft 50 as a rotation axis.

The rotation adjustment unit 70 is formed with coupling protrusion 701 that is fitted into the opening 108 of the main body 10. Ball plungers 703 may be arranged on the coupling protrusion 701 at a constant interval. The opening 108 may be formed at one end of the main body 10 connected to the shaft 50 and recesses corresponding to the ball plungers 703 may be formed inside the opening 108.

The rotation adjustment unit 70 needs to fix the shaft 50 when no rotational operation force is applied to the shaft 50. The ball plungers 703 serve to fix the shaft 50 so as not to be rotated when external force applied to the shaft 50 has a predetermined intensity or less.

According to the exemplary embodiments of the present invention, an endoscope will be inserted for identification of positions of ribs and precise surgery for multiple rib fracture, and two or three topical incisions, each having a diameter of 2 cm or less for insertion of the endoscope, are made at both lateral sides of the chest. In this case, the drill unit 30 and the shaft 50 of the medical motor drill 1 or 1' may be inserted through any one incision that is regardless of insertion of the endoscope.

In general, during thoracic cavity surgery, one lung is subjected to ventilation to acquire a space inside the thoracic cavity. As such, a screwing space of the shaft 50 and the drill unit 30 is acquired. In addition, as the shaft 50 is extendable up to a length of 15 cm or more, positioning the drill unit 30 at any of all ribs inside the adult thoracic cavity is possible via adjustment in the angle of the medical motor drill 1 or 1'. When a lip plate is inserted into the thoracic cavity through either incision at both lateral sides of the chest, the angle of the drill unit 30 may be adjusted such that the drill unit 30 is oriented perpendicular to the inserted lip plate to tighten a screw to the lip plate for correcting the rib.

Through provision of the medical motor drill 1 or 1', the angle of which is adjustable in various ways at the outside of the thoracic cavity, a plurality of ribs may be corrected even through a single incision in the case of multiple rib fracture. In addition, correction of the ribs may be accomplished only using a topical incision owing to the small diameters of the drill unit 30 and the shaft 50.

EXPLANATION OF REFERENCE NUMBER OF DRAWINGS

1,1': medical motor drill 10: main body
101: handle 103: switch
105: battery 107: power source
108: opening 302: connector
30: drill unit 301: motor
303: drill blade 305: cap
307: drill tip 40: conductor
50: shaft 60,60': angle adjustment unit
601: toothed gear 70: rotation adjustment unit
701: coupling protrusion 703: Ball plunger
80: drive force transmission unit 801,801': driving gear
802: driven drum 803: wire
805,805': stopper 807: worm gear
8071: additional gear 3021: protective packing

What is claimed is:

1. A medical motor drill comprising:
   a main body;
   a shaft connected to the main body;
   a drill unit connected to the shaft so as to be bendable relative to the shaft, the drill unit including a motor configured to receive power from the main body and a drill blade configured to be rotated by the motor;
   a drive force transmission unit configured to bend the drill unit relative to the shaft; and
   an angle adjustment unit connected to the drive force transmission unit to adjust a bending degree of the drill unit,
   the shaft includes a rotation adjustment unit coupled to the main body to rotate the shaft about a longitudinal axis of the shaft as a rotation axis.

2. The medical motor drill according to claim 1, wherein the drive force transmission unit includes:
   a driving gear configured to be rotated by the angle adjustment unit;
   a driven drum connected to the drill unit; and
   a wire wound around the driving gear and the driven gear.

3. The medical motor drill according to claim 2, wherein the driving gear includes a worm gear.

4. The medical motor drill according to claim 2, wherein the drive force transmission unit further includes a stopper configured to be selectively fitted to a groove of the driving gear.

5. The medical motor drill according to claim 1, wherein the angle adjustment unit is located at the main body.

\* \* \* \* \*